United States Patent [19]

Kidwell

[11] Patent Number: 4,902,627
[45] Date of Patent: Feb. 20, 1990

[54] METHOD FOR DETECTING AMINE-CONTAINING DRUGS IN BODY FLUIDS BY SIMS

[75] Inventor: David Kidwell, Alexandria, Va.

[73] Assignee: The United States of America as represented by the Secretary of the Navy, Washington, D.C.

[21] Appl. No.: 698,476

[22] Filed: Feb. 5, 1985

[51] Int. Cl.$^4$ ............................................. G01N 27/62
[52] U.S. Cl. ..................................... 436/112; 436/96; 436/98; 436/111; 436/173
[58] Field of Search ..................... 250/282; 436/91, 92, 436/93, 96, 98, 173, 111, 112

[56] References Cited

U.S. PATENT DOCUMENTS

| | | | |
|---|---|---|---|
| 4,005,291 | 1/1977 | Arsenault | 250/282 |
| 4,259,572 | 4/1981 | Brunnee et al. | 250/281 |
| 4,296,322 | 10/1981 | Wechsung | 250/282 |
| 4,378,499 | 4/1983 | Spangler et al. | 250/287 |

OTHER PUBLICATIONS

Hunt et al., Anal. Chem., vol. 50, No. 13, pp. 1781–1784, 1978.
Cooks et al.; Laser Desorption, SIMS, and Oher Forms of Desorption Ionization ASMS Jun. 1982, pp. 585–590.
Busch et al.; SIMS: Application to Biomolecules ASMS Jun. 1982, pp. 388–389.
Scheifers et al.; Molecular SIMS; American Lab. Mar. 1982, pp. 19–33.
S. E. Unger et al., "Identification of Quartenary Alkaloides in Mushroom by Chromatography/Secondary Ion Mass Spectrometry", Anal. Chem. 1981, 53, 976–981.
Bush and Cooks, Mass Spectrometry of Large, Fragile, and Involatile Molecules, Science, V. 281, 15 Oct. 1982.
Ross, Kidwell, and Colton, Selective Detection of Aldehydes and Ketones by Derivatization/Secondary Ion Mass Spectrometry, 32nd Annual Conference on Mass Spectrometry, San Antonio, Tex., 27 May–1 Jun. 1984.
Kidwell, Ross, and Colton, Sequencing of Peptides by Secondary Ion Mass Secondary Ion Mass Spectrometry, J. Am. Chem. Soc., 2219–2220, 4 Apr. 1984.
K. L. Busch et al., "Desorption Ionization Mass Spectrometry:Sample Preparation for Secondary Ion Mass Spectrometry, Laser Desorption and Field Desorption", J. Am. Chem. Soc., 1982, 104, pp. 1507–1511.

*Primary Examiner*—Robert J. Hill, Jr.
*Attorney, Agent, or Firm*—Thomas E. McDonnell; A. David Spevack

[57] ABSTRACT

A method of analyzing a sample for selected molecules which consists of reacting the molecule with a reagent that produces a charged derivative which can be desorbed and analyzed using Secondary Ion Mass Spectrometry (SIMS).

6 Claims, 12 Drawing Sheets

FRAGMENTATION OF PROPOXYPHENE
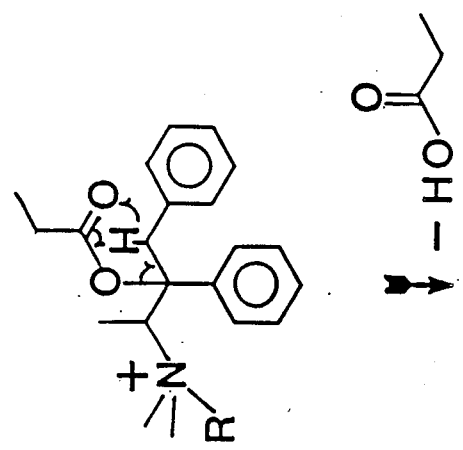
| | m/z |
|---|---|
| R = H | 340 |
| R = CH$_3$ | 354 |
| R = CD$_3$ | 357 |
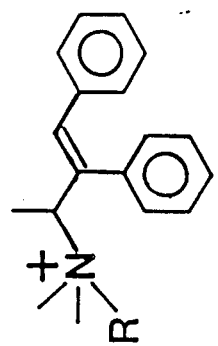
| | m/z |
|---|---|
| R = H | 266 |
| R = CH$_3$ | 280 |
| R = CD$_3$ | 283 |
*FIG. 11*

4,902,627

METHOD FOR DETECTING AMINE-CONTAINING DRUGS IN BODY FLUIDS BY SIMS

BACKGROUND OF THE INVENTION

This invention pertains generally to mass spectrometry analysis techniques and more particularly to secondary ion mass spectrometry (SIMS) analysis techniques.

Gas chromatography coupled with mass spectrometry (GC/MS) is often the method used to analyze mixtures of organic compounds. The compounds are separated after volatilizing the molecules in the gas chromatrographic process and identified using mass spectrometry. The separation is necessary to purify the components and, thus, reduce interference in the mass spectrometric technique. This technique works well for small, volatile molecules that can easily withstand the temperatures necessary to vaporize the molecule without being thermally degraded. However, large, involatile, thermally fragile molecules, particularly enzymes, proteins, drugs, and other similar molecules of biological interest, can not be analyzed using this technique because they would be degraded by the heat necessary to volatilize the molecules for the chromatography process.

Other methods have also been used to produce molecules which can be analyzed using MS. Electron ionization (EI) produces a positive ion radical by stripping away an electron from the parent molecule The molecular ion and its fragments give a mass spectrum characteristic of the molecule. Similarly, Munson and Field, *Chemical Ionization Mass Spectrometry*, 88 J. Am. Chem. Soc. 2621 (1966), analyzed molecules using a chemical ionization (CI) technique which used ions, particularly protons, to generate molecular species which could be analyzed using mass spectrometry CI and EI, however, generally require that the ionizing agent act on gas-phase molecules. Thermally fragile molecules required the development of new methods which would allow mass spectrometric analysis without degrading the molecule.

New techniques permitting analysis of large, involatile, and thermally fragile molecules have recently been developed. Mass spectrometric analysis was accomplished by directly desorbing the molecular ions from the solid or liquid phase. This eliminated the need to vaporize the molecules or ions thus reducing thermal degradation. This general technique, termed desorption ionization (DI), has lead to the discovery of several additional desorption methods These include secondary ion mass spectrometry (SIMS), fast-atom bombardment (FAB), plasma desorption (PD), field desorption (FD), electrohydrodynamic ionization (EMHS) and thermal desorption. These techniques are reviewed and further defined in Busch and Cooks, *Mass Spectrometry of Large, Fragile, and Involatile Molecules*, 218 Science 247 (1982).

SIMS, the subject of the present invention, desorbs and ionizes molecules in the solid form or mixed with a solid matrix using energetic ions. Low fluxes of ions are used for surface analysis of organic molecules thus avoiding ion degradation of the molecules. Higher fluxes are used for inorganic compounds or for depth profiling. SIMS, therefore, provides a highly sensitive method of analysis for large, volatile, thermally fragile molecules. The experiment is simple compared to GC/MS and other techniques. The samples analyzed can often be observed for hours under low flux bombardment.

Desorption of ions from the solid matrix requires that ions be generated, usually by ion impact, fission particle impact, laser irradiation, chemical manipulation, and similar techniques. These methods, however, are limited by their lack of specificity for particular molecules that may be in a mixture. Ion impact, fission particle impact, laser irradiation, and similar techniques ionize the molecule they contact, whether it be the molecule of interest or another molecule. Similarly, chemical manipulation, principally accomplished by the addition or removal of a proton, is non-specific and affects any molecule with a protonated functional group. Novel methods of selectively ionizing a molecule of particular interest could, therefore, greatly increase the efficacy of the SIMS technique.

SUMMARY OF THE INVENTION

It is, therefore, an object of the present invention to provide a method for selectively ionizing target molecules.

It is a further object of the present invention to analyze the ionized target molecules using SIMS.

It is another object of the present invention to eliminate interference with SIMS from other molecules in the sample by selectively ionizing only target molecules.

These and other objects are achieved by derivatizing target molecules to produce target molecules having an ionic moiety. The derivatized target molecules are desorbed from the sample and analyzed using SIMS. Non targeted molecules, of little interest, are not derivatized and, therefore, are not desorbed as ions and do not interfere with the SIMS analysis. Other objects, advantages, and novel features of the present invention will become apparent from the following detailed description of the invention.

(a) shows the fragmentation pattern for a mixture of low molecular weight ($C_2$–$C_5$) aldehydes and ketones, where Peak No. 1 represents acetaldehyde, Peak No. 2 represents acrolein, Peak No. 3 represents acetone, Peak No. 4 represents butyraldehyde, and Peak No. 5 represents cyclopentanone.

(b) shows the fragmentation pattern for a mixture of medium molecular weight ($C_5$–$C_8$) aldehydes and ketones, where Peak No. 6 represents 2-pentanone, Peak No. 7 represents 3-hexanone, Peak No. 8 represents 3-heptanone, and Peak No. 9 represents 3-octanone.

(c) shows the fragmentation pattern for a mixture of high molecular weight ($C_6$–$C_{17}$) aldehydes and ketones, where Peak No. 10 represents cyclohexanone, Peak No. 11 represents benzaldehyde, Peak No. 12 represents cinnamaldehyde, Peak No. 13 represents 9-phenanthrene-carboxaldehyde, and Peak No. 14 represents 1-pyrene-carboxaldehyde.

Figure 3:
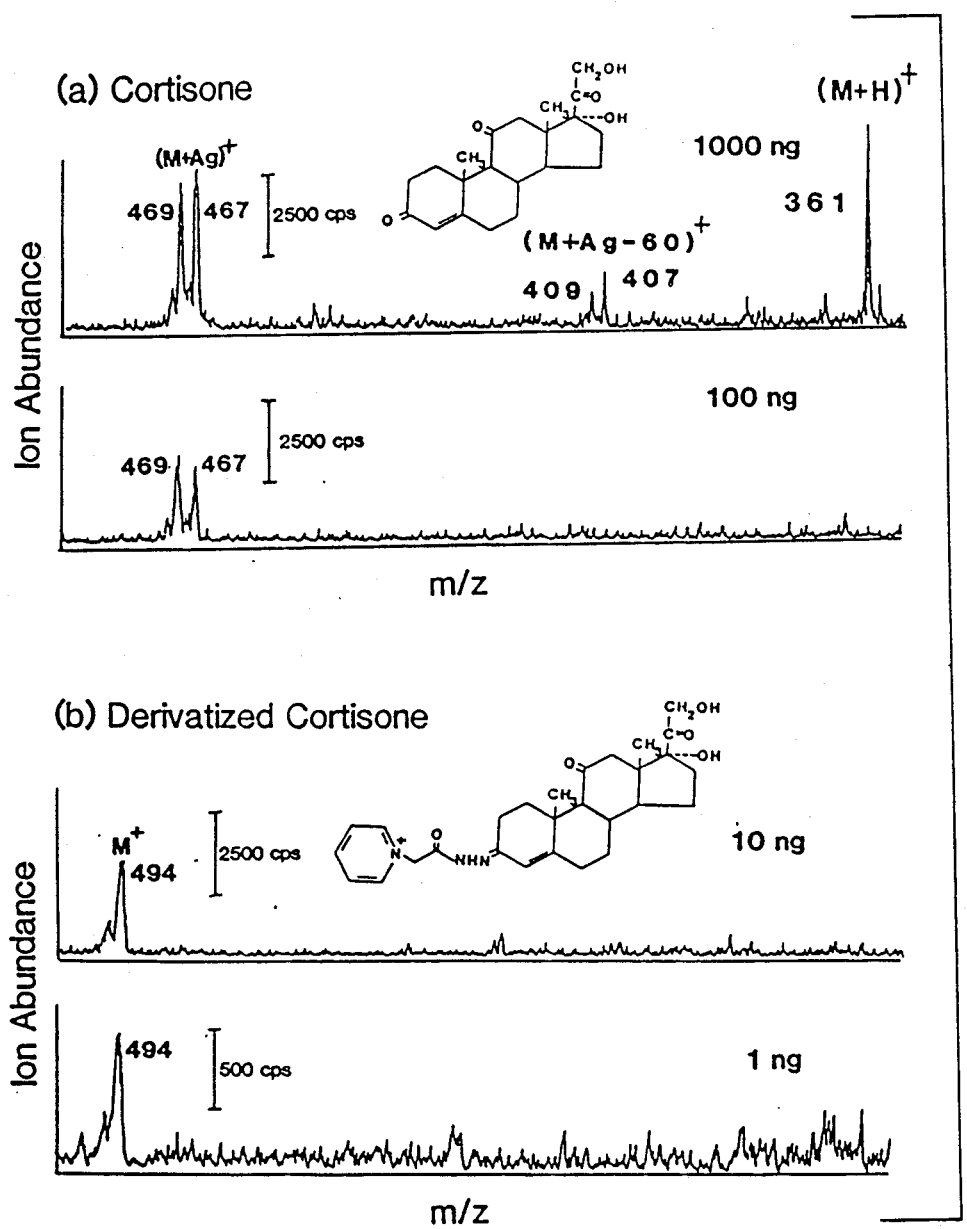

FIG. 3 is a fragmentation pattern showing SIMS spectra of (a) underivatized cortisone and (b) derivatized cortisone.

Figure 4:
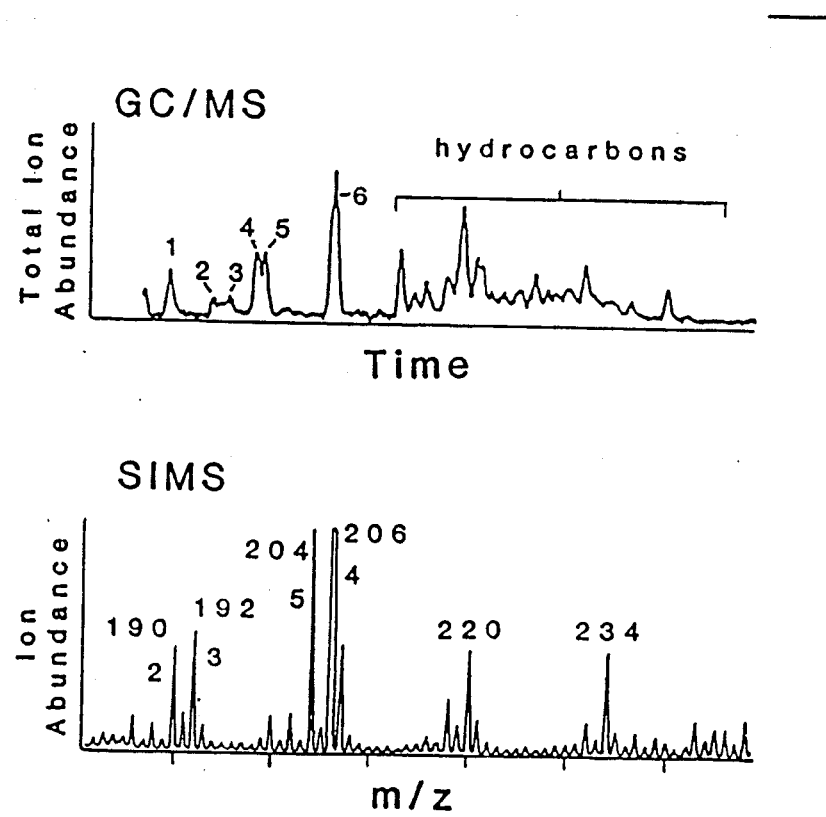

FIG. 4 is a fragmentation pattern showing a comparison of GC/MS analysis with drivatization/SIMS analysis of paint vapors (peak #:compound, 1:butene, 2:2-propenal, 3:2propanone, 4:2-methyl propanal, 5:2-methyl propenal, 6:benzene).

Figure 5:

FIG. 5 is a fragmentation pattern showing SIMS spectra of three active ingredients in a Sin-U-Tab ™ tablet derivatized to observe only the phenyltoloxamine at m/z 270.

Figure 6:
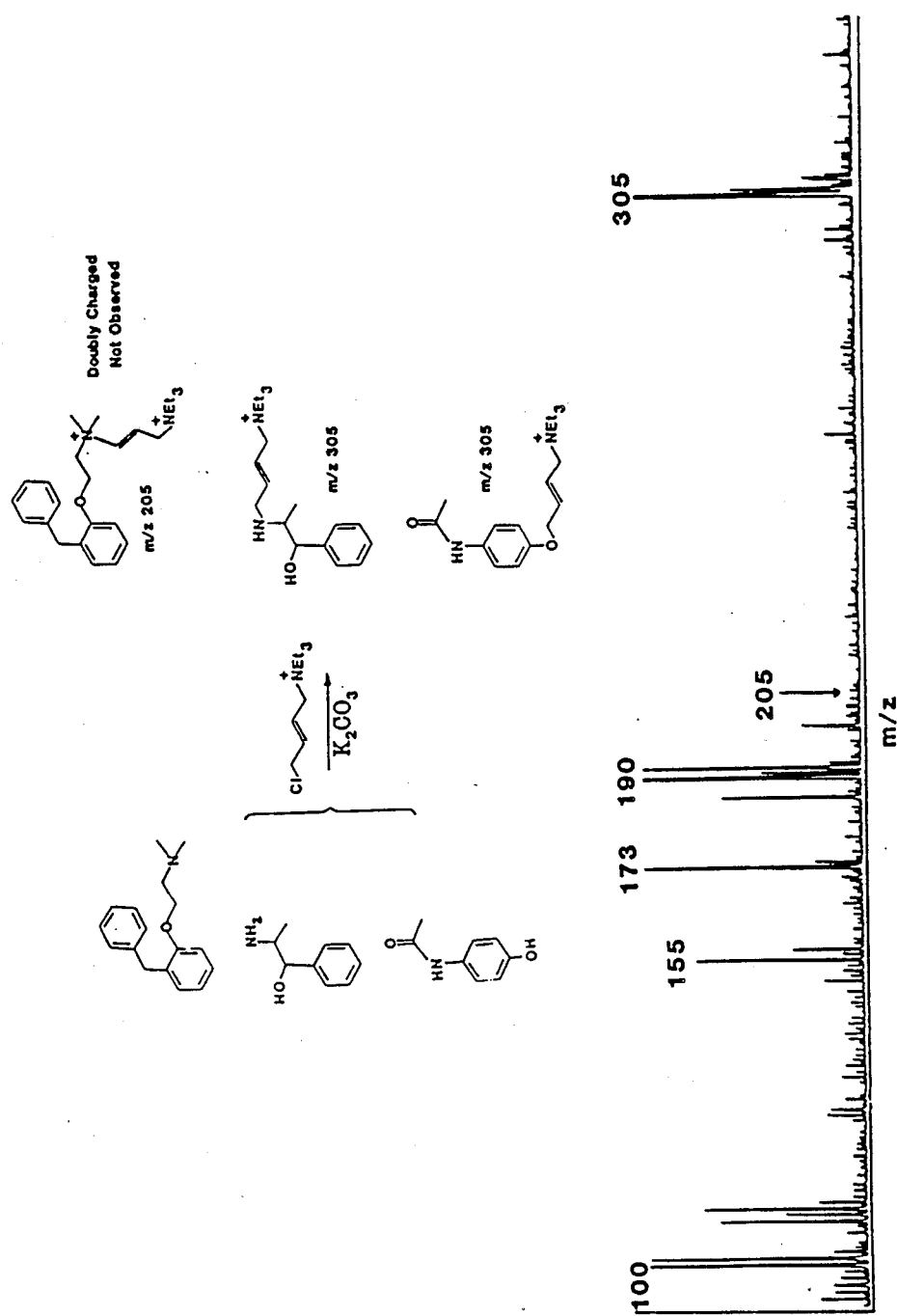

FIG. 6 is a fragmentation pattern showing SIMS spectra of three active ingredients in a Sin-U-Tab# tablet derivatized to observe only the norpseudoephedrine and acetaminophen at m/z 305.

Figure 7:
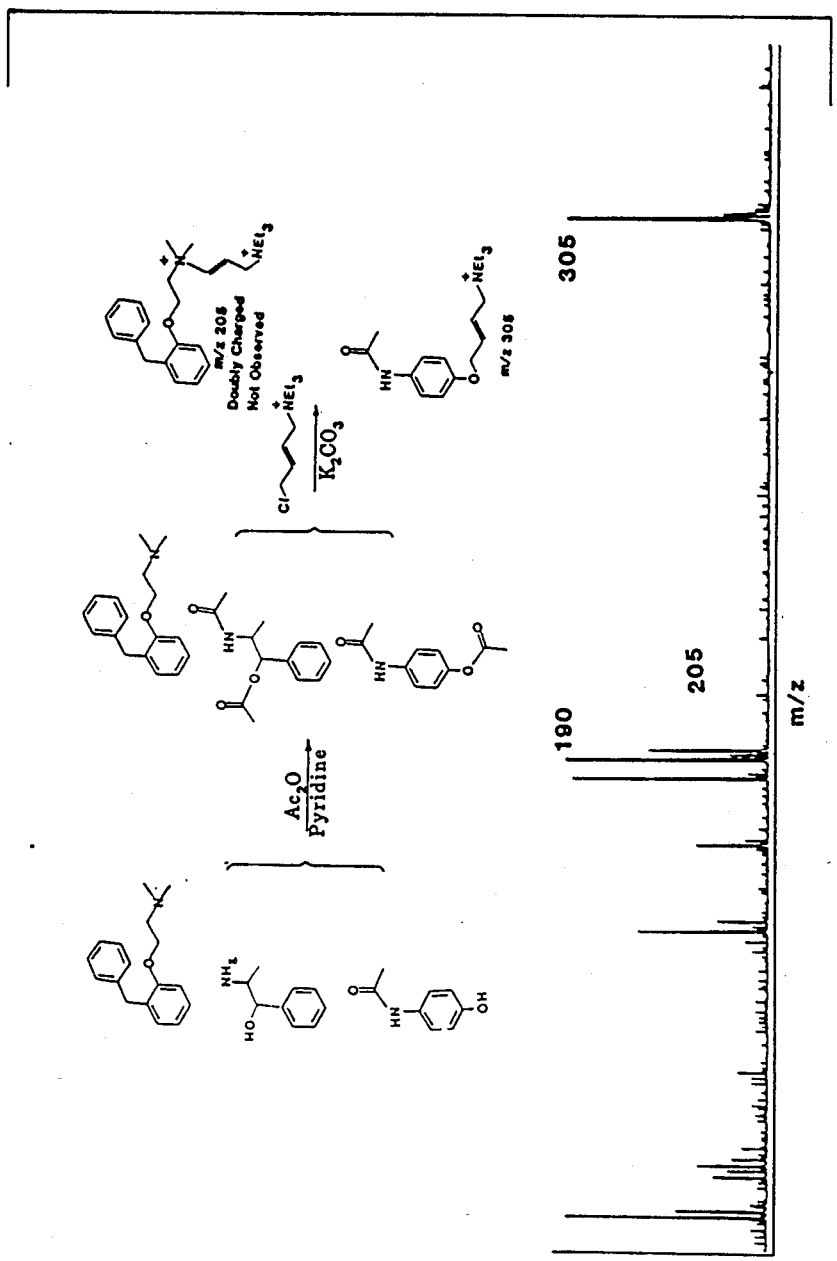

FIG. 7 is a fragmentation pattern showing SIMS spectra of three active ingredients in a Sin-U-Tab# tablet derivatized to observe only the acetaminophen at m/z 305.

Figure 8:
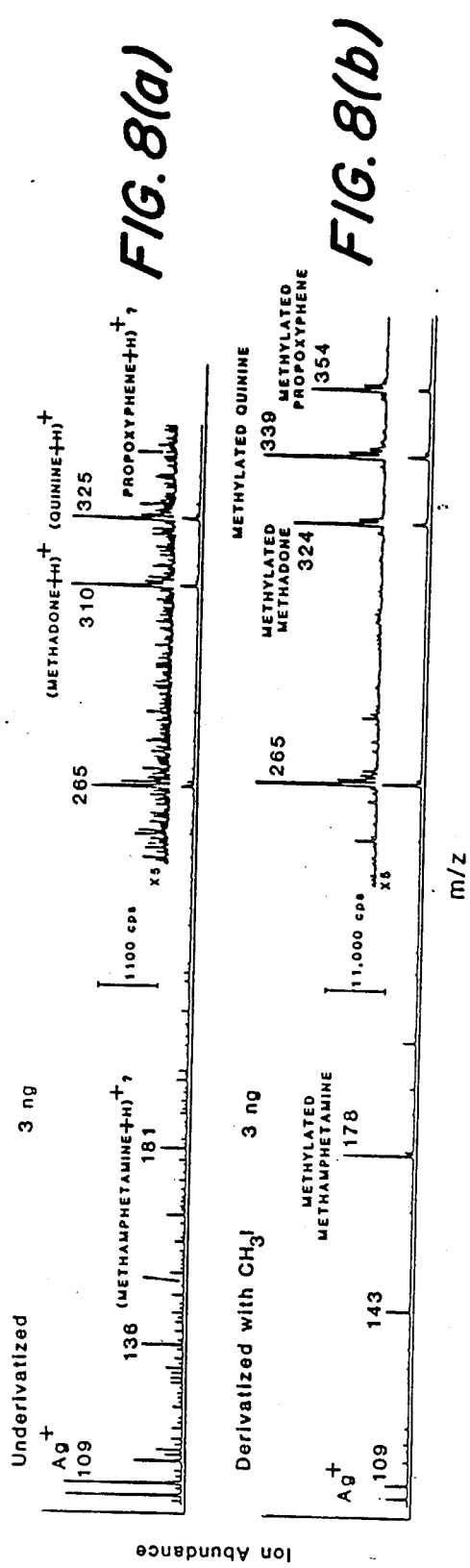

FIG. 8 is a fragmentation pattern showing SIMS spectra of an equal mixture by weight of methamphetamine, methadone, quinine and propoxyphene in human urine (a) underivatized and (b) derivatized.

Figure 9:
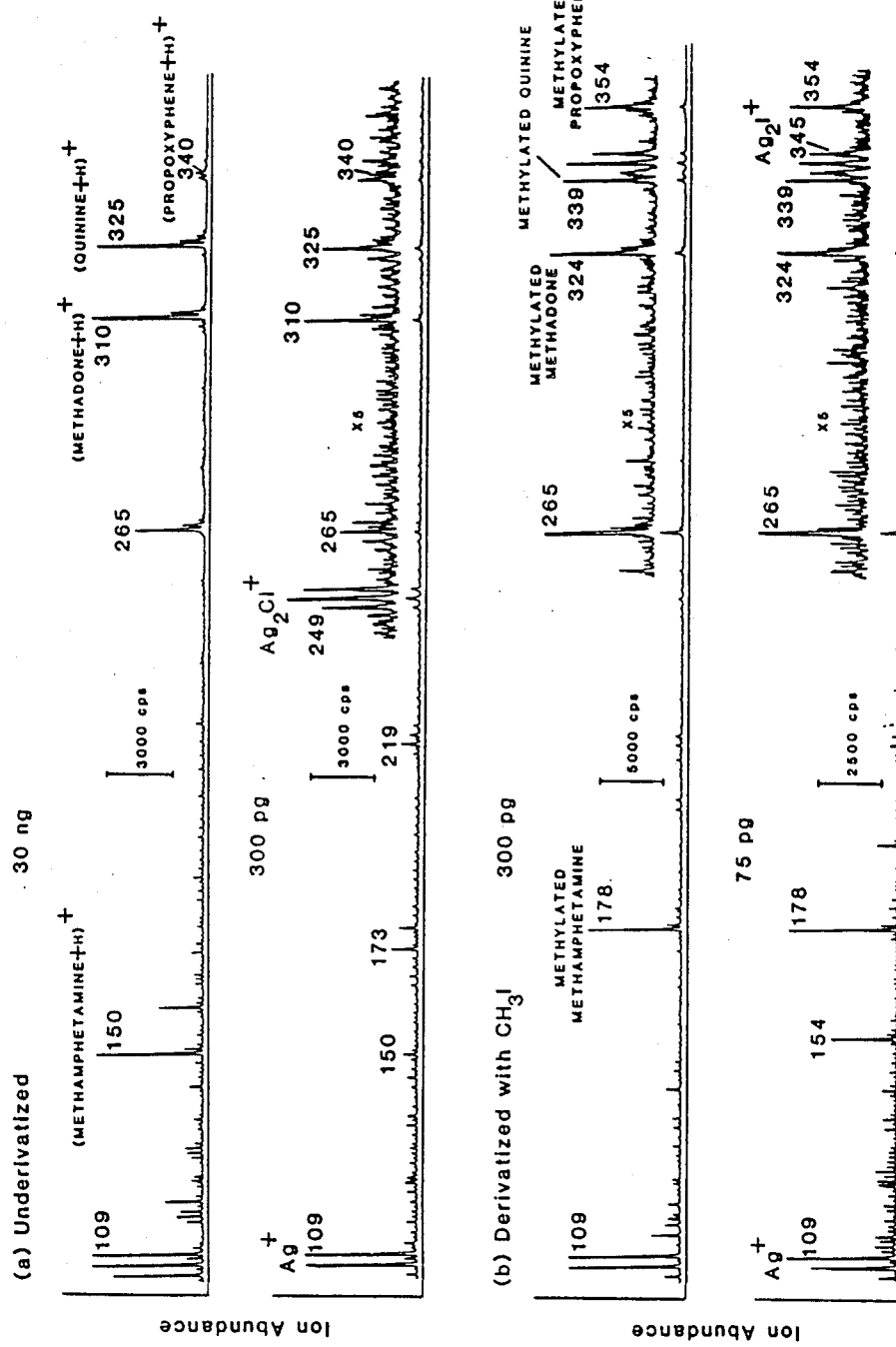

FIG. 9 is a fragmentation pattern showing SIMS spectra of an equal mixture by weight of methamphetamine, methadone, quinine and propoxyphene in water at various concentrations, both (a) underivatized and (b) derivatized with $CH_3I$.

Figure 10:
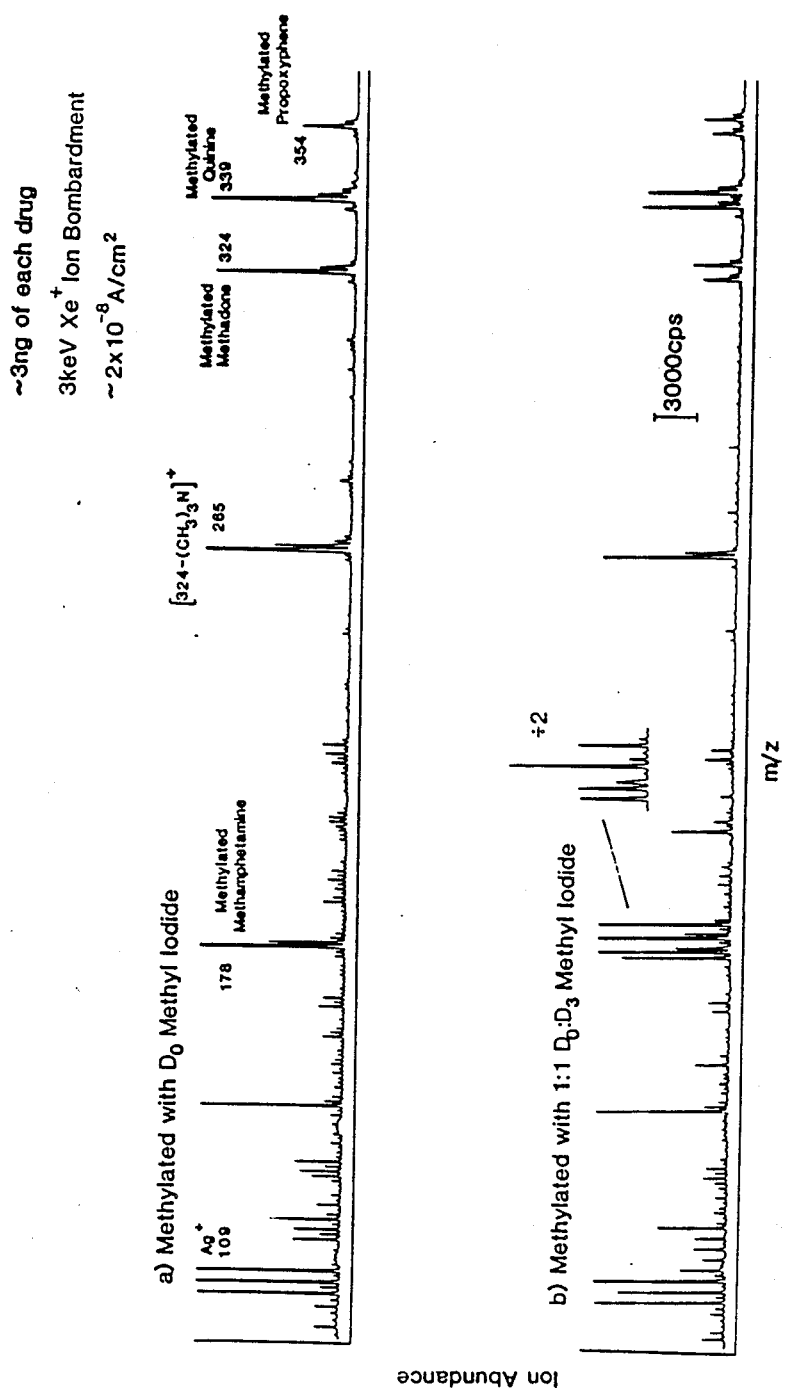

FIG. 10 is a fragmentation pattern showing SIMS spectra of an equal mixture by weight of methamphetamine, methadone, quinine and propoxyphene in water derivatized with (a) iodomethane and (b) a 1:1 mixture of d0:d3-iodomethane.

FIG. 11 is an equation showing fragmentation of propoxyphene via a McLafferty rearrangement.

Figure 12:
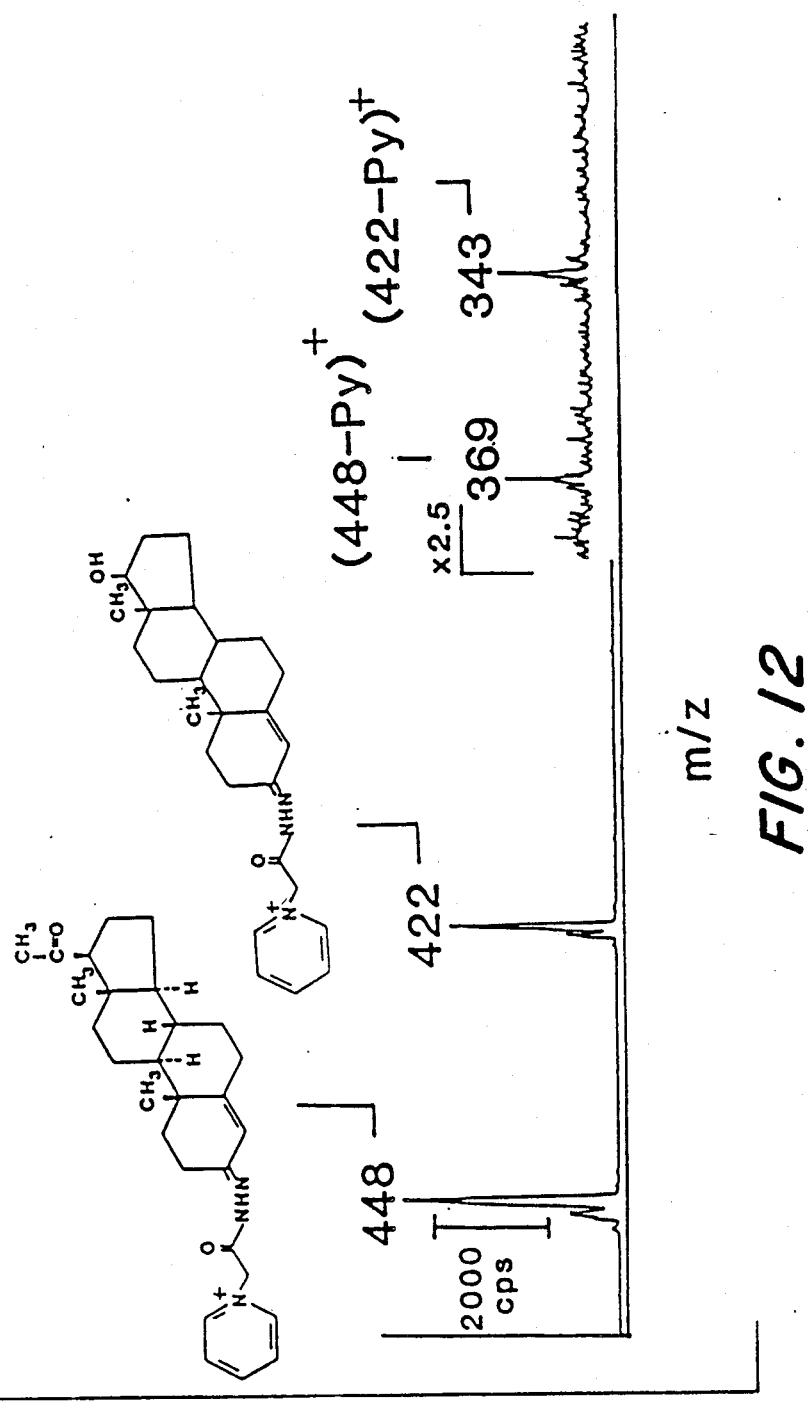

FIG. 12 is a fragmentation pattern showing SIMS spectra of progesterone and testosterone derivatized with Girard's Reagent P.

DESCRIPTION OF THE INVENTION

In the present invention, a target molecule that is to be analyzed by SIMS but that is contained in a sample matrix is derivatized by selective chemical agents which produce a charged derivative The resulting mixture of derivatized target molecules and nonderivatized sample molecules is coated on a surface compatible with the SIMS technique, acid etched silver foil being the preferred surface, placed in the mass spectrometer and bombarded with energetic particles. This produces a large secondary ion yield from only the derivatized molecules. The derivatized target molecules are readily detected with little or no interference from the noncharged sample molecules.

The particles used for bombardment can be any particle commonly used in SIMS such as $Xe^o$, $Ar^o$, $Xe^+$, and $Ar^+$, $Xe^+$ being preferred. The particle beam has an energy range from about 1–10 keV and a current density from about 1–150 $nA/cm^2$, a 2 keV beam having a current density of 10 $nA/cm^2$ being preferred.

The charged derivatives useful in the present invention include but are not limited to those produced from functional groups such as amines, carboxylic acids, ketones, alcohols, aldehydes, and phenols. Derivatizing reagents include but are not limited to acyl chlorides, alkyl halides, particularly iodomethane, and sulphonyl chlorides. Basically, any molecule which has a functional group which can be derivatized can be analyzed using this technique. Adding protons to produce charged groups is possible but is not preferred because of its nonselectivity.

Figure 1:
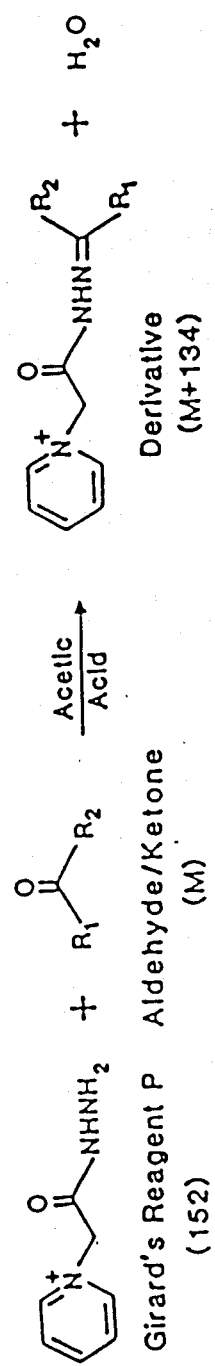
FIG. 1 is an equation showing the reaction mechanism for carbonyl compounds with Girard's Reagent P.
Figure 2:
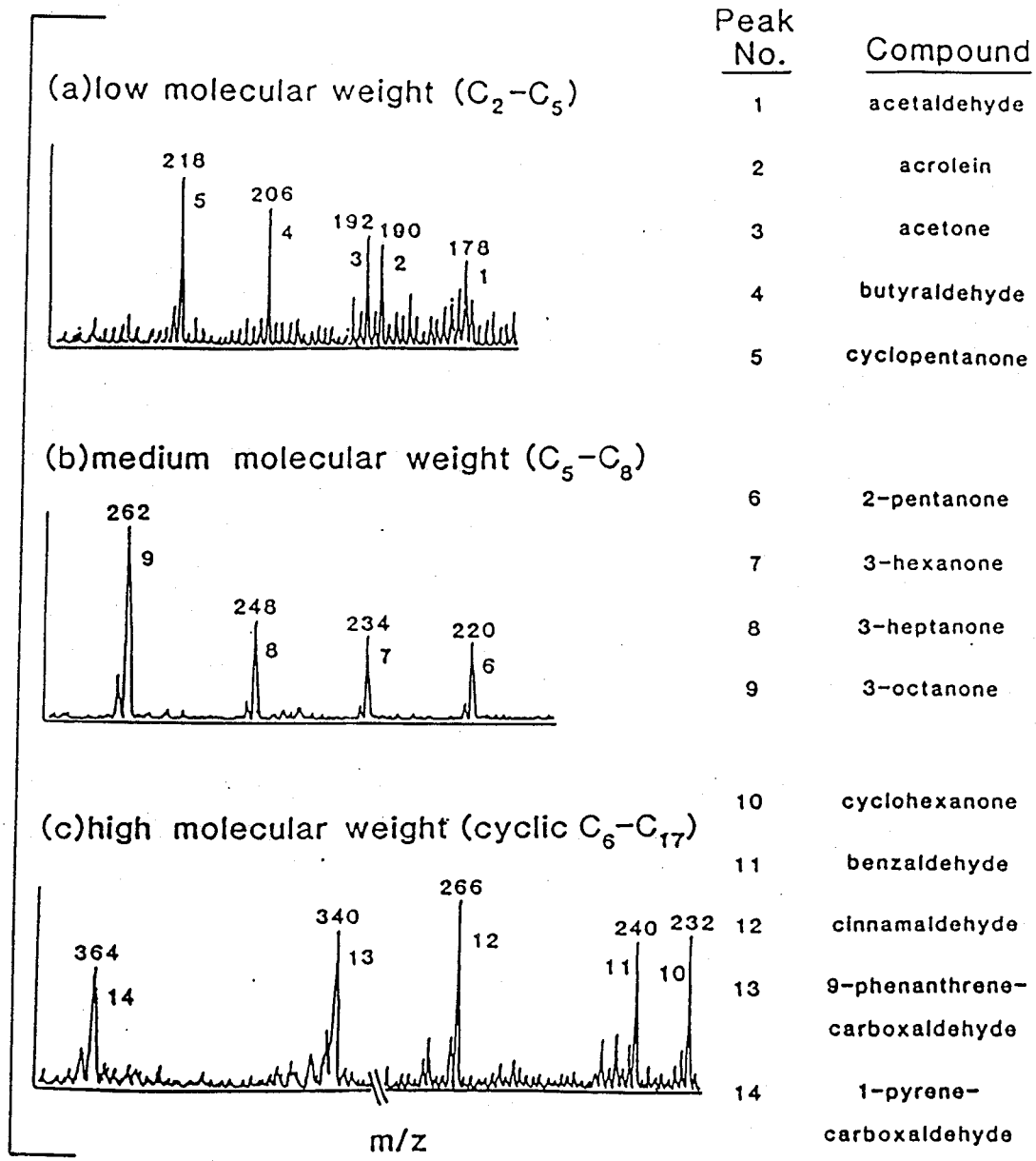
FIG. 2 is a fragmentation pattern showing SIMS spectra of three mixtures of aldehydes and ketones, 2 ng each on silver, derivatized with Girard's Reagent P.

Carbonyl-containing compounds, particularly aldehydes and ketones, were analyzed by dissolving the compound in 10 mL of 50:50 ethanol/water solutions to concentrations of 1–10 micrograms/mL. To these mixtures approximately 10 mg of Girard's Reagent P (1-(carboxymethyl) pyridinium chloride hydrazide) and 10 microliters of acetic acid were added. Carbonyl-containing compounds react with Girard's Reagent P to produce a derivatized hydrazone containing a quarternary ammonium group ion which is detected at [M+134]+ where M is the molecular weight of the carbonyl containing compound. The reaction for aldehydes and ketones and other carbonyl-containing compounds is illustrated in FIG. 1. Samples were prepared for SIMS analysis by the deposition of 1 microliter of the aldehyde/ketone derivative solution onto acid-etched silver foil Samples were bombarded with a 2-keV Xe+ rastered ion beam of approximately 10 $nA/cm^2$-current density.

Highly volatile carbonyl compounds such as acetaldehyde, acetone, and acrolein that are not observed by conventional SIMS can be derivatized and analyzed readily using the above method. The less volatile aldehydes and ketones such as pyrene- and phenanthrenecarboxaldehydes do not yield abundant molecular ions and, therefore, are difficult to analyze using SIMS. They do produce adduct ions with silver and these adduct ions can be analyzed using SIMS but only in the microgram range. However, using the above method, the derativized molecules can be observed in the nanogram range In fact, all of the derivatized carbonyl-containing compounds studied could be detected at the low nanogram level.

Steroids such as progesterone, testosterone, and cortisone have been derivatized and analyzed with this method. Cortisone was chosen to demonstrate the enhanced sensitivity obtained with the derivatization/SIMS technique. The results of a comparison of the SIMS spectra of underivatized and derivatized cortisone are presented in FIG. 3. The ions that were observed from cortisone include the molecular ion [M+H]+ (m/z 361), the silver cationized ion [M+Ag]+ (m/z 467 and 469), and the fragment ion at m/z 407 and 409 corresponding to the loss of the $HOCCH_2OH$ group. With 100 ng of cortisone only [M+Ag]+was observed. The SIMS spectra of derivatized cortisone show a single peak corresponding to the molecular ion of the derivatized species and a low abundance of the same fragmentation.

Because quaternary ammonium salts exhibit high ionization yields and because they exhibit low fragmentation, derivatization dramatically enhances the sensitivity of SIMS. The derivatized cortisone was detected at 10 ng with the same signal-to-noise ratio as that for 100 ng of underivatized cortisone, which is approximately an order of magnitude improvement in the detection sensitivity.

In addition to analyzing solid and liquid samples, airborne vapor molecules were analyzed using this technique. The atmosphere containing the vapor molecules was pumped through an impinger immersed in a solution selected to dissolve the contaminant vapor molecule. The solution containing the dissolved contaminant was analyzed using the technique described above for liquid samples.

The derivatization/SIMS technique was used to analyze vapors given off from various paints when heated This study was conducted when shipyard workers complained of eye, throat, and lung irritations. The traditional analytical method used to collect and analyze airborne contaminants consisted of concentration of the gaseous species on an adsorbent followed by thermal desorption and GC/MS analysis of the desorbed compounds. Acrolein, or 2-propenal, a known lachrymator, was suspected. The subject method was applied to the analysis of acrolein and other aldehydes or ketones that may be given off from the paints.

Vapors given off from the paints were drawn, by a pump, through an impinger that contained 10 mg Girard's Reagent P and 10 microliters acetic acid in 10 mL of a 50:50 ethanol/water solution The vapors were sampled for approximately 30 minutes as the paints were heated from ambient to greater than 300° C. For the SIMS analysis, 1 microliter of the impinger solution was deposited on silver and analyzed A comparison of GC/MS and SIMS analysis is presented in FIG. 4.

The results of the GC/MS analysis as indicated in the total ion abundance profile show numerous compounds present in the air sample. Some peaks such as those corresponding to butene and benzene are well resolved whereas others are not. Acrolein was identified (peak #2) but could not be separated from other co-eluting compounds. The SIMS analysis confirmed the presence of acrolein (molecular weight=56) by the detection of an ion at m/z 190 that was identified as the Girard's Reagent P derivative of acrolein. In addition, not only are all of the aldehydes and ketones that were observed by GC/MS detected by SIMS; but other aldehydes and ketones are observed, also. Conversely, those compounds such as the hydrocarbons that appear in the GC/MS trace are not observed in the SIMS spectra since they do not contain carbonyl functional groups and were not derivatized. Thus, the derivatization/-SIMS method provides selectivity and enhancement of the signal from targeted compounds with respect to that of unwanted or matrix species This method complements and corroborates the GC/MS analysis very well.

The method of the present invention can also be used to analyze a sample for amines In particular, drugs containing an amine functional group can be analyzed when contained in body fluids such as urine, saliva or blood serum. Opiates such as morphine, codiene and heroin; amphetamines such as amphetamine, methamphetamine, and mescalin; barbiturates such as diphenylhydantoin and barbital; LSD; and cocaine and metabolites of cocaine (benzoylecgonine) are examples of drugs having amine functional groups which can be analyzed using the present method.

Sin-U-Tab ® is a common antihistamine composed of three active ingredients: phenyltoloxamine, norpseudoephedrine and acetaminophen (FIG. 5) as well as binders and coloring agents. If the mixture of compounds is acylated with acetic anhydride, all primary and secondary amines and phenols will be acylated. If the mixture is then quaternized with iodomethane, only the tertiary amines will react. Since SIMS is relatively insensitive to noncharged species, only the quaternized tertiary amine species will be observed. FIG. 5 shows the resultant spectra. Only the products from phenyltoloxamine at m/z 270 and ions from the citric acid binder were observed It should be emphasized that the reactions were done on a mixture without purifying the intermediates.

Likewise, if slightly different chemistry is employed to derivatize the mixture with a charged alkylating agent, all amine groups and phenols will be alkylated (FIG. 6). Since phenyltoloxamine is a tertiary amine, alkylation with a charged alkylating agent will produce a doubly charged ion that is not readily observed by SIMS. Further alkylation of the product from norpseudoephedrine to produce a doubly charged species is controlled by the reaction time. The singly-alkylated products from norpseudoephedrine and acetaminophen both appear at n/z 305. Presumably, they could be distinguished by reaction with acetic anhydride. This would react with the product from norpseudoephedrine and not acetaminophen. This charged alkylating agent has also been used to derivatize and detect barbiturates.

Finally, only the acetaminophen can be observed by acylation and alkylation of the mixture with a charged alkylating agent (FIG. 7). Acyl phenols are unstable to base. Hydrolysis regenerates the phenol which can then be alkylated. The SIMS spectrum of this mixture shows only the derivative of acetaminophen.

The technique of the present invention can also be used to analyze for stimulants and analgesics in aqueous media or human urine. Normal human urine contains few charged impurities. FIG. 8a shows SIMS spectra of an equal mixture by weight of four drugs in human urine. Protonated molecular ions of quinine and methadone are observed whereas ions from methamphetamine and propoxyphene are not observed. Addition of acid (HCl) to the urine before depositing it on a silver surface did not allow the observation of molecular ions from methamphetamine or propoxyphene.

FIG. 8b shows the same urine sample derivatized using iodomethane. In this spectrum all four drugs are observed. In this case the molecular ion of methamphetamine is the most intense species rather than absent as in the underivatized spectrum Over and above observing some species that were absent, derivatization increases the absolute signal intensity of all the molecular ions.

FIG. 9 demonstrates the enhancement achieved by derivatization. In this case, the drugs were in an aqueous media. The derivatized drugs can be observed at the 300 pg level with the same signal-to-noise ratio as the underivatized drugs at the 3000 pg level.

Other drugs such as morphine, codeine, amphetamine and methamphetamine have ben detected by derivatizing with iodomethane. Cocaine could not be derivatized under the conditions that we employed and was only detected as the protonated molecular ion. Iodomethane-d3 can be used to distinguish between methamphetamine and amphetamine and between morphine and codeine.

Since most of the species observed by SIMS are even electron ions, they show very little fragmentation compared to odd electron ions formed by electron impact ionization. When fragmentation does occur in SIMS, it is primarily by loss of neutral molecules as in chemical ionization. Of course, lack of fragmentation is an ideal situation for quantitation since the ion intensity is concentrated in very few peaks, thereby enhancing the sensitivity.

Derivatized methadone is an example of a compound that shows loss of a neutral molecule. Fragmentation of derivatized methadone is responsible for the abundant ion intensity at m/z 265 corresponding to loss of trimethylamine. The structural feature responsible for this loss is unclear at this time. The fragment ion does not shift in mass when iodomethane-d3 is used as the derivatizing agent which shows that the loss is trimethylamine. Presumably if the loss were a direct cleavage, the fragmentation would produce a secondary cation. Derivatized methamphetamine also contains a similar 2-propylammonium group and yet shows little or no loss of trimethylamine to produce an ion at m/z 119. Therefore, a rearrangement during fragmentation probably occurs in the case of methadone.

McLafferty rearrangements are low energy, facile processes that produce losses of neutral molecules. Propoxyphene undergoes such a rearrangement (FIG. 10). This produces the ion at m/z 266 by loss of the elements of propanoic acid. The ion intensity is only about 20% of the molecular ion intensity. It shows the appropriate shift to m/z 269 when propxyphene is derivatized with iodomethane-d3.

In a mixture of drugs from a somewhat complex matrix such as urine, one would like to confirm the structure of the ion, since one may have ions that are isobaric Therefore, the drug mixture in FIG. 11 was derivatized with a 50:50 mixture of d0:d3-iodomethane to help locate the ions of interest The molecular ions can readily be distinguished from the background due to their doublet patterns. Also, methamphetamine gives the characteristic 1:1:1 pattern indicating that two methyl groups were added.

Another example of selective detection is the use of reagents that reacts with only one type of functional group. For example, Girard's reagents (ammoniumacylhydrazides) react with ketones and aldehydes to form hydrazones. This reaction, as discussed earlier, has been used to derivatize steroids that contain a keto functionality and carbonyl containing pollutants. An example of the increase in sensitivity upon derivatization of cortisone can be seen in FIG. 4. As in the example of the drug mixture, the increase in sensitivity is about a factor of ten with a similar signal-to-noise ratio.

Other steroids have been studied such as progesterone and testosterone with similar results. Good signals of several thousand counts per second can be obtained on 1–10 ng amounts as shown in FIG. 12.

In the derivatization of cortisone and progesterone, the much higher reactivity of the unsaturated keto group in ring A has been relied upon to avoid derivatization with two charged groups As in the example with phenyltoloxamine, multiple derivatization would decrease sensitivity. The lack of reactivity of the other keto groups in steroids was shown by the constant secondary ion signal intensity for products reacted for various times and in the presence of a large excess of Girard's Reagent P.

In conclusion, derivatization/SIMS has been demonstrated to enhance the detection of selected compounds from complex mixtures. Prior extraction and concentration with this technique is not necessary for drug screening, for example, as it may be for GC/MS studies. This technique can analyze relatively non-volatile materials such as steroids without degradation. It also produces mostly molecular ions which aid in quantitation.

Attachment of a charged group by chemical derivatization to organic compounds with a particular functional group allows selective and sensitive analysis of those species by SIMS. Matrix effects are reduced so that parameters such as pH and impurity levels have little or no effect on the secondary ion emission of the quaternary ammonium salt derivatives.

The method described is of comparable sensitivity relative to tandem mass spectrometry (MS/MS). It is able to detect materials at the 1 nanogram level, or approximately 1 ppm, with decidedly less complex instrumentation. Although, in certain applications, the capabilities of the derivatization/SIMS method could be enhanced further when combined with MS/MS. For example, because the SIMS spectra of quaternary ammonium salts exhibit low fragmentation, MS/MS may be used to induce more fragmentation and confirm the structures of unknown compounds.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Carbonyl Derivatization

Carbonyls, including aldehydes and ketones, were dissolved in 10 mL of 50:50 ethanol water solutions to concentrations of 1–10 $\mu$g/mL. To these mixtures approximately 10 mg of Girard's Reagent P (1-(carboxymethyl) pyridinium chloride hydrazide), and 10 microliters of acetic acid were added. Carbonyl containing compounds react as described in the equation in FIG. 1. One microliter of the derivitized sample was deposited onto acid etched silver foil. The sample was bombarded with a 2-keV Xe+ rastered ion beam of approximately 10 nA/cm$^2$ current density and the SIMS spectra taken.

EXAMPLE II

Drug/Amine Derivatization

The amine or drug was dissolved in 50% water/methanol or 50% urine/methanol. The solution was made basic using potassium carbonate (10mg/ml solution). To the basic solution was added about 20 mg iodomethane. The solution either was let stand at room temperature for two hours or heated for five minutes to 60° C. In either case, it became homogeneous. After derivatization, the sample was analyzed as for the carbonyl compounds.

EXAMPLE III

Selective Derivatization

A Sin-U-Tab tablet was crushed and approximately 5 mg of material was used for each analysis. The three principal ingredients in this tablet are phenyltoloxamine, norpseudoephedrine and acetaminophen If the sample is first acylated with acetic anhydride, all primary and secondary amines and phenols will be acylated If this mixture is then quaternized with iodomethane as in example II, only the phenyltoloxamine will react, be derivatized and observed in the SIMS experiment.

If this mixture is quaternized with iodomethane as in example II, both the phenyltoloxamine and the norpseudoephedrine will react and be detected in the SIMS experiment.

If the mixture is first aclyated and then reacted with 4-triethylammonium-1-chloro-2-butene in a basic media both the acetaminophen and phenyltoloxamine will react. However, only the acetaminophen will form a mono-cation salt and be detected in the SIMS experiment.

Acylation of the Mixture

Approximately 5 mg of the crushed tablet was reacted with 50:50 acetic anhydride:pyridine. The material only partially dissolved. The excess aclyating reagent was removed in a stream of nitrogen Reaction with 4-triethylammonium-1-chloro-2-butene The residue from the acylated mixture was partially dissolved in 1 mL of 50% methanol/water. Potassium carbonate (10mg) and 4-triethylammonium-1-chloro-2-butene (10 mg) were added. The mixture was heated at 60° C. for 5 minutes and analyzed by SIMS as for the aldehydes in example I.

Preparation of 4-triethylammonium-1-chloro-2-butene

To a 250 mL round bottom flask equipped with magnetic stirrer, was added 25 g (0.2 moles) of 1,4-dichloro-2-butene and 100 mL of methanol. Then 10 g (0.1 moles) of triethylamine was slowly added. The solution was stirred at room temperature for 2 hours and concentrated on a rotovap to a white solid. The residual 1,4-dichloro-2-butene was removed under a vacuum. The salt showed a strong molecular ion at m/z 190 and m/z 192 in the SIMS spectra. The salt was used without further purification.

EXAMPLE IV

Derivatization of Barbiturates

An aqueous solution of the Barbiturates was adjusted to pH about 10 using potassium hydroxiode. An excess of 4-trimethylammonium-1-chloro-2-butene was added. The solution was heated at 60° C. for 3 minutes and then analyzed as for the aldehydes.

The techniques of the present invention can be used to selectively analyze almost any derivatized molecule but are particularly useful for analyzing for carbonyl and amine containing drug or drug metabolites in urine or blood serum. The technique has also been sued to analyze for carbonyl containing compounds in the atmosphere, particularly where painting is being done.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of analyzing for an amine-containing drug in a body fluid, comprising the steps of:
   pre-selecting the drug which is to be analyzed for in said body fluid;
   admixing said body fluid with a solvent to form a sample wherein any said pre-selected drug contained in said body fluid is dissolved in said solvent;
   acylating said sample with an acylating reagent to acylate any primary and secondary amines contained in said sample;
   adding an alkyl group to any said pre-selected drug in the sample by quaternizing any said pre-selected drug in the sample with a quaternizing reagent or alkylating any said pre-selected drug in the sample with a charged alkylating reagent to form an ionic derivative of any quantity of said pre-selected drug contained in said sample, thereby forming a derivatized sample;
   depositing said derivatized sample upon a surface compatible with secondary ion mass spectrometry analysis techniques;
   bombarding said derivatized sample with a particle beam to desorb any ionic derivative contained in said derivatized sample thereby forming a bombarded sample; and
   analyzing said bombarded sample to determine the quantity of any desorbed ionic derivative using secondary ion mass spectrometry.

2. The method of claim 1 wherein said body fluid is selected from the group consisting of urine, saliva and serum.

3. The method of claim 1 wherein said surface is acid-etched silver foil.

4. The method of claim 1 wherein any ionic derivative is desorbed by bombarding said derivatized body fluid with a 1-10 keV particle beam of about 1-150 nA/cm$^2$ [nA/cm$^2$]current density.

5. The method of claim 4 wherein any ionic derivative is desorbed by bombarding said derivatized body fluid with a 2 keV Xe$^+$ rastered ion beam of about 10 nA/cm$^2$ current density.

6. The method of claim 1 wherein said acylating reagent is acetic anhydride.

* * * * *